US006451331B1

(12) United States Patent
Slavtcheff et al.

(10) Patent No.: US 6,451,331 B1
(45) Date of Patent: Sep. 17, 2002

(54) PLEATED COSMETIC EFFERVESCENT CLEANSING PILLOW

(75) Inventors: Craig Stephen Slavtcheff, Guilford, CT (US); Joanna Hong Zhang, Milford, CT (US); Alexander Paul Znaiden, Trumbull, CT (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 33 days.

(21) Appl. No.: 09/651,005

(22) Filed: Aug. 29, 2000

Related U.S. Application Data

(60) Provisional application No. 60/179,295, filed on Jan. 31, 2000.

(51) Int. Cl.⁷ ................................................. A61K 9/70
(52) U.S. Cl. ...................... 424/404; 424/401; 424/402
(58) Field of Search ................................ 424/404, 401, 424/402

(56) References Cited

U.S. PATENT DOCUMENTS

| 1,808,834 A | 6/1931 | Busch |
| 2,560,649 A | 7/1951 | Hornaday |
| 3,242,093 A | 3/1966 | Compton |
| 4,025,628 A | 5/1977 | Dewey et al. |
| 4,234,442 A | 11/1980 | Cornelissens |
| 4,272,393 A | 6/1981 | Gergely |
| 4,291,685 A | 9/1981 | Taelman |
| 4,311,606 A | 1/1982 | Kaeser |
| 4,515,703 A | 5/1985 | Haq |
| 4,592,855 A | 6/1986 | Gioffre et al. |
| 4,600,620 A | 7/1986 | Lloyd |
| 4,601,938 A | 7/1986 | Deacon et al. |
| 4,603,069 A | 7/1986 | Haq et al. |
| 4,643,939 A | 2/1987 | Sugiyama et al. |
| 4,666,707 A | 5/1987 | Eguchi et al. |
| 4,745,021 A | 5/1988 | Ping, III et al. |
| 4,791,097 A | 12/1988 | Walele et al. |
| 4,808,322 A | 2/1989 | McLaughlin |
| 4,886,387 A | 12/1989 | Goldberg et al. |
| 4,941,990 A | 7/1990 | McLaughlin |
| 5,006,339 A | 4/1991 | Bargery et al. |
| 5,041,233 A | 8/1991 | Kutny et al. |
| 5,100,674 A | 3/1992 | Ser et al. |
| 5,198,198 A | 3/1993 | Gladfelter et al. |
| 5,306,439 A | 4/1994 | Lockhart |
| 5,338,476 A | 8/1994 | Pancheri |
| 5,342,535 A | 8/1994 | Ramirez et al. |
| 5,352,387 A | 10/1994 | Rahman et al. |
| 5,431,841 A | 7/1995 | Lockhart |
| 5,560,873 A | 10/1996 | Chen et al. |
| 5,578,562 A | 11/1996 | Lockhart |
| 5,605,749 A | 2/1997 | Pike et al. |
| 5,607,681 A | 3/1997 | Galley et al. |
| 5,683,976 A | 11/1997 | Colurciello, Jr. et al. |
| 5,714,451 A | 2/1998 | Brouwer et al. |
| 5,718,729 A | 2/1998 | Harris |
| 5,720,949 A | 2/1998 | Davis |
| 5,955,057 A | 9/1999 | Maunder et al. |
| 6,063,390 A | * 5/2000 | Farrell et al. ................ 424/404 |

FOREIGN PATENT DOCUMENTS

| EP | 343069 | 5/1989 |
| EP | 343070 | 5/1989 |
| EP | 0 339 276 | 11/1989 |
| FR | 2 398 671 | 7/1977 |
| JP | 62045519 | 2/1987 |
| WO | 97/43366 | 11/1997 |
| WO | 99/48469 | 9/1999 |
| WO | 00/07561 | 2/2000 |

OTHER PUBLICATIONS

International Search Report.

* cited by examiner

*Primary Examiner*—Alton Pryor
(74) *Attorney, Agent, or Firm*—Milton L. Honig

(57) ABSTRACT

A wiping article is provided which includes an effervescent cleanser composition held within a sachet, at least one wall of the sachet including at least one pleat. The presence of pleats allows expansion room within the sachet to accommodate effervescent action. It also results in an ergonomically pleasant pillow configuration. Advantageously, the sachet is formed of two sheets with the second sheet being relatively more rigid than the first sheet and non-pleated which permits easier graspability by a user's hand. Additionally, at least one of the sheets should be water permeable. In a preferred embodiment, the effervescent composition is an intimate mixture of an acid material such as citric acid and an alkaline material such as sodium bicarbonate. Water contact causes the combination to effervesce. Skin benefit agents may be included within the composition.

10 Claims, 2 Drawing Sheets

PLEATED COSMETIC EFFERVESCENT CLEANSING PILLOW

This application derives priority under 35 U.S.C. §112(e) from U.S. Provisional Application S/No. 60/179,295 filed Jan. 31, 2000.

BACKGROUND OF THE INVENTION

1. Field of the Invention

The invention concerns an effervescent foaming article for body cleansing that imparts a pleasant sensory feel to a user's skin.

2. The Related Art

Classically the process of cleansing skin has employed a surfactant composition. Sometimes an implement has joined the composition. Implements such as sachets serve multipurposes. One function is as a delivery package for the surfactant. Sachets may also assist in generating foam. They further function as an abrasive assisting in cleansing the skin.

An early example of cleansing pad technology is found in U.S. Pat. No. 1,808,834 (Busch Sr.). A fabric pouch is disclosed surrounding a cleansing composition mainly consisting of calcium and sodium carbonate.

U.S. Pat. No. 4,234,442 (Cornelissens) describes a sachet which can consist of a water permeable material filled with an acidic and an alkaline constituent. Adipic, succinic and glutaric acids exemplify the acidic constituent. Sodium bicarbonate and carbonate represent the alkaline ingredient.

U.S. Pat. No. 4,272,393 (Gergely) describes a cleaning article formed of a porous flexible substrate, especially a cellulosic paper, impregnated with detergent and a gas-generating system. The latter is formed by separating an acidic component such as citric acid from a basic component such as sodium carbonate in two separate areas of the substrate.

U.S. Pat. No. 4,515,703 (Haq), U.S. Pat. No. 4,600,620 (Lloyd et al.) and U.S. Pat. No. 4,603,069 (Haq et al.) all describe wiping articles impregnated with surfactant. These do not contain any effervescent ingredients.

WO 97/43366 (Askew et al.) reports an effervescent system to improve dispensability of granular laundry detergent powders into wash water of automatic washing machines. Citric acid and bicarbonate combinations are employed to generate effervescence.

Most of the effervescent sachet technology has been directed at the cleaning of fabrics. Some of the publications have referred to personal care applications involving skin or hair. Yet there has been very little elaboration on sachet construction focused on the challenges of personal care applications. Unlike sachets thrown into a washing machine, personal care involves actual hand contact during the effervescent process. Sachets as they billow from the effervescent process fail to hold shape integrity. Under rubbing conditions they assume a nondescript, mushy pliable configuration. Effervescent gases also appear highly constrained to the confining space of the pre-activation dry volume.

It is an object of the present invention to provide a cleansing article such as a sachet which during effervescent activation maintains a relatively constant shape under conditions of rubbing against the skin.

Another object of the present invention is to provide a cleansing article such as a sachet containing an effervescent system activated by contact with water wherein the article is constructed with expandable pocket areas to accommodate billowing from gas generation.

Still a further object of the invention is to provide a cleansing article such as a sachet which imparts a pleasant sensory feel in a user's hand, especially a toilet bar shape, at a time prior, during and after use against the skin.

It is to be noted that the subsequently described invention is broader than the objects or technical problems it is directed to solve.

SUMMARY OF THE INVENTION

A cosmetic article is provided for cleansing body surfaces, the article including:

a sachet having at least one water permeable wall, the sachet being sealed along all its perimeter, at least one pleat formed in at least one wall of the sachet; and an effervescent cleanser composition positioned within the sachet.

Advantageously, the effervescent cleanser composition is in the form of an anhydrous dry solid having the composition including:

(i) from about 1 to about 80% of an alkaline material;

(ii) from about 0.5 to about 80% of an acid material; and (iii) from about 0.1 to about 30% of a surfactant.

Also provided is a method for cleansing skin involving wetting with water a cosmetic article, generating foam from the article and wiping skin surfaces with the wetted article, the article being a pleated sachet filled with the effervescent cleanser composition delineated above.

BRIEF DESCRIPTION OF THE DRAWINGS

The above features, advantages and object of the present invention will more fully be appreciated through the following detailed discussion, reference being made to the drawing in which.

DETAILED DESCRIPTION OF THE INVENTION

Figure 1:
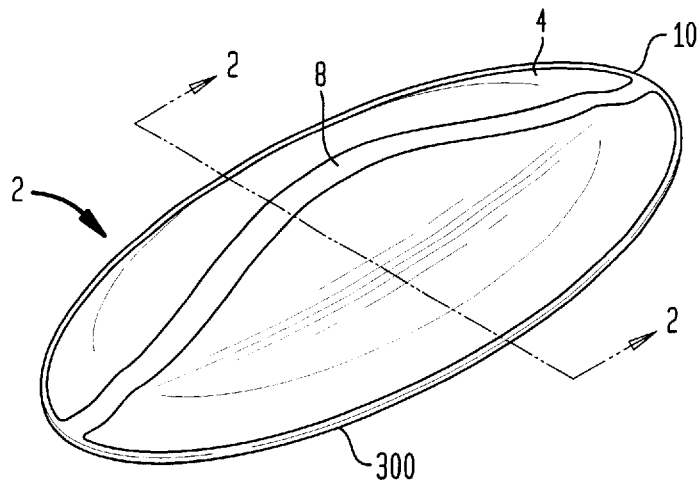
FIG. 1 is a perspective view of a first embodiment of the article according to the present invention.

Cosmetic wiping articles of the present invention when contacted with water billow to many times (more than 10 but often more than 40 times) their dry size when activated by water. The effervescent cleansing system exudes copious amounts of lather. A plumped "pillow" arises from the effervescent action. By careful control of the acidic and alkaline components, a squeaky clean rinsed feeling is felt on a user's skin.

Now it has been discovered that maximum billowing can be achieved by use of one or more pleats on at least one of the walls that define the sachet. Pleats are preferably double folded segments of a wall pressed together in place with capacity for expansion to a volume greater than its original folded volume. Where the sachet is formed of two walls or sheets, preferably the at least one pleat will be formed on only one of those two walls. Advantageously, the non-pleated second wall is constructed of a material more rigid than the material forming the pleated first wall. Rigidity may be imparted in any of a number of ways. Where both sheets are of woven or non-woven fibers, the more rigid sheet can be formed of denser fibers, a greater number of fibers, extra fiber layers, different fiber material, different patterned arrangement or any combination thereof. The more rigid sheet can also be achieved through different chemistry or binders, increased coating amount and penetration, binding or bonding method and pattern, porous structure, physical texture and thickness, and degree of bonding. A particularly preferred combination is that the first, pleated wall is formed of a spun lace wood pulp polyester non-woven fabric while the rigid second wall is a polypropylene melt blown substrate. The number of pleats may range anywhere from 1 to about 200, preferably from 1 to about 50, optimally from 1 to about 20 per sheet.

Where the non-pleated wall is more rigid than the pleated one, the former functions to maintain a relatively non-billowing face of the article while allowing gaseous expansion on the opposite side of the article through the first pleated wall. It is much more ergonomically friendly in a user's hand. Moreover, the combination of flexible and relatively rigid walls provides for easier grippability and prevents slippage from the grasp. A further advantage is that the billowed first wall can express cleansing surfactant against the skin while the more rigid wall can be applied to areas requiring a rough surface to exfoliate skin.

At least one of the sachet walls must be water permeable. Suitable materials for forming the walls are rayon, polyester, polyethylene, polypropylene, cotton or any fiber combination thereof. These sheets may be woven or non-woven. Cellulosic paper fiber Substrates are best not employed because of their insufficient wet-strength although they may be blended with other fibers referenced above; it is important that the substrate sheets are not readily torn open through consumer rubbing of the article. Unlike laundry sachet articles, those of the present invention should not rupture which would cause dispersion of their granular contents into wash water. Rather it is intended for all cleanser composition components to exit by dissolution through the permeable walls of the sachet.

Figure 2:
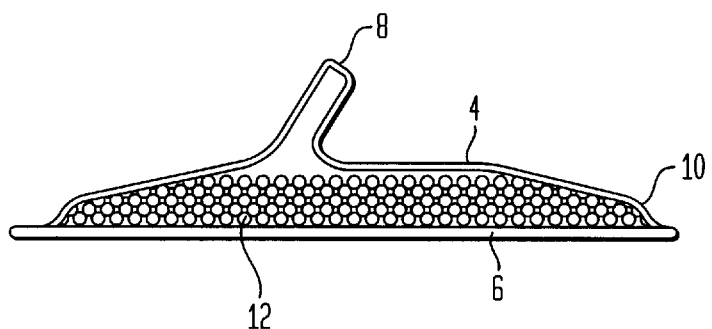
FIG. 2 is a cross-sectional view along line 2—2 of FIG. 1 of the first embodiment.

FIGS. 1 and 2 illustrate a first embodiment of the present invention. Sachet 2 is formed of a first relatively flexible wall 4 activation and a relatively rigid wall 6. These walls are joined along their outer perimeters by a heat seal 10. Alternative sealing mechanisms could also be employed such as stitching or even forming both walls from a unitary substrate with the sealed perimeter merely being a fold. Wall 6 on its outer surface is patterned with a series of raised areas. These assist in gripping, improve rigidity and assist in exfoliation of the skin. An effervescent cleanser composition 12 is positioned within the pouch. Pleat 8 unfolds during effervescent action of the composition allowing for an outward expansion of wall 4 so as to provide more internal volume for expanding effervescent gases.

Figure 3:
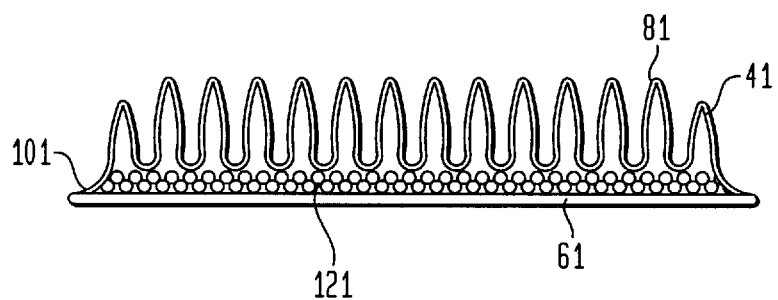
FIG. 3 is a cross-sectional view of a second embodiment according to the present invention showing a multiplicity of pleats.

FIG. 3 illustrates a second embodiment wherein a flexible first wall 41 is pleated with numerous pleats 81. A backing or rigid second wall 61 is placed opposite the first wall. A heat seal 101 along the perimeter of the walls seals the pouch enclosing an effervescent cleanser composition 121.

Figure 4A:
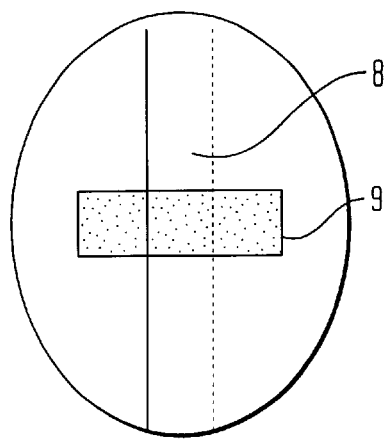
FIG. 4a is a plan view of an exterior surface of a single pleated wall of a sachet.
Figure 4B:
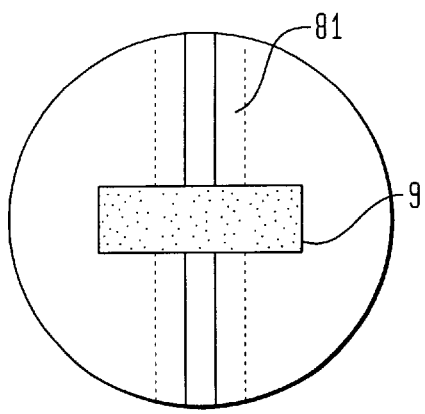
FIG. 4b is a plan view of an exterior surface of a two-pleated wall of a sachet.
Figure 4C:
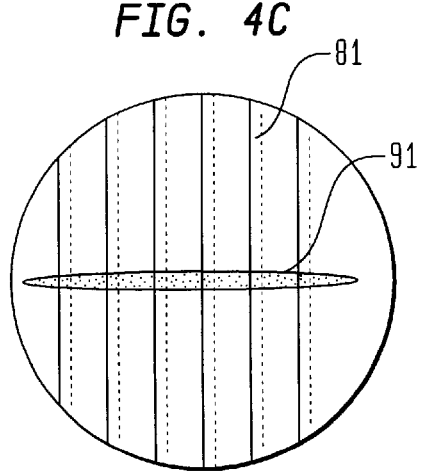
FIG. 4c is a plan view of an exterior surface of a multiply-pleated wall of a sachet.

FIG. 4a illustrates from an exterior view outward a wall of a sachet having a single pleat. In one manufacturing process, the pleat 8 is held in place by an adhesive tape 9 during the sachet assembly process. The pleated wall is positioned over a non-pleated substrate dosed with a pile of cleanser composition and followed by a heat sealing to enclose the composition within the juxtaposed substrates. Thereafter the Adhesive tape is removed. FIG. 4b is a view similar to that of FIG. 4a except illustrating multiple pleats 81 held in place for manufacturing purposes only by an adhesive tape FIG. 4c is an external view of a pleated wall with the multiple pleats 81 being held for manufacturing purposes only by a glue track 91. A further but un-illustrated method of maintaining pleats is use of spot welds at each end of the pleat.

A preferred embodiment of the present invention to achieve effervescence is a combination of an alkaline material and an acid material. Thus, in the preferred embodiment a first component of compositions within the sachet is that of an alkaline material. The alkaline material is a substance which can generate a gas such as carbon dioxide, nitrogen or oxygen, i.e. effervesce, when contacted with water and the acidic material. Suitable alkaline materials are anhydrous salts of carbonates and bicarbonates, alkaline peroxides (e.g. sodium perborate and sodium percarbonate) and azides (e.g. sodium azide). Preferably the alkaline material is sodium or potassium bicarbonate. Amounts of the alkaline material may range from about 1 to about 80%, preferably from about 5 to about 49%, more preferably from about 15 to about 40%, optimally from about 25 to about 35% by weight of the total composition.

In the preferred embodiment, a second important component within the sachet is that of an acidic material. Suitable for this purpose are any acids present in dry solid form. Especially appropriate are $C_2$–$C_{20}$ organic mono- and polycarboxylic acids and especially alpha-and beta-hydroxycarboxylic acids; $C_2$–$C_{20}$ organophosphorus acids such as phytic acid; $C_2$–$C_{20}$ organosulfur acids such as toluene sulfonic acid; and peroxides such as hydrogen peroxide. Typical hydrocycarboxylic acids include adipic, glutaric, succinic, tartaric, malic, maleic, lactic, salicylic and citric acids as well as acid forming lactones such as gluconolactone and glucarolactone. Most preferred is citric acid. Also suitable as acid material may be encapsulated acids. Typical encapsulating material may include water soluble synthetic or natural polymers such as polyacrylates (e.g. encapsulating polyacrylic acid), cellulosic gums, polyurethane and polyoxyalkylene polymers. By the term "acid" is meant any substance which when dissolved in deionized water at 1% concentration will have a pH of less than 7, preferably less than 6.5, optimally less than 5. These acids preferably at 25° C. are in solid form, i.e. having melting points no less than 25° C. Concentrations of the acid should range from about 0.5 to about 80%, preferably from about 10 to about 65%, optimally from about 20 to about 45% by weight of the total composition.

By the term "anhydrous" is meant the presence of no more than about 10%, preferably no more than 5% and optimally no more than 1% water by weight of the total composition. Water of hydration is not considered to be water for purposes of the anhydrous definition. However, it is preferred to minimize, preferably to eliminate any water of hydration.

Advantageously the combined amount of acidic and alkaline materials will be at least about 1.5%, preferably from about 40 to about 95%, optimally from about 60 to about 80% by weight of the total composition.

Another preferred component of compositions according to the present invention is that of a surfactant, preferably a dry surfactant solid at 20° C. Most suitable for the present invention is sodium cocoyl isethionate. Other useful surfactants include sodium methyl cocoyl taurate and sodium lauryl sulfate. Surfactants may be of the anionic, cationic, nonionic, amphoteric, zwitterionic varieties and combinations thereof. Amounts of the surfactant may range from about 0.1 to about 30%, preferably from about 1 to about 30%, optimally from about 8 to about 15% by weight of the total composition.

A variety of skin benefit agents may be included to improve afterfeel properties. Advantageously these substances will be available as anhydrous dry powders. Alternatively these substances may be liquids deposited upon or into a powdered substrate (e.g. sodium bicarbonate or zeolite) to achieve a resultant dry flowing powder. Within the skin benefit agent scope are several categories of materials. These include emollients, antiaging actives, antibacterials and fungicides, skin lighteners, sunscreens and combinations thereof. Amounts of the skin benefit agents may range from about 0.001 to about 30%, preferably from about 0.1 to about 20%, more preferably from about 0.5 to about 10%, optimally between about 1 and about 5% by weight of the total composition.

Emollients may be in the form of natural or synthetic esters, silicone oils, hydrocarbons, starches, fatty acids and mixtures thereof. Typically the emollient may range in concentration from about 0.1 to about 35% by weight of the total composition.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms.

Linear volatile silicone materials generally have viscosities less than about 5 centistokes at 25° C. while cyclic materials typically have viscosities of less than about 10 centistokes.

Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C.

Among the ester emollients are:
(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.
(2) Ether-esters such as fatty acid esters of ethoxylated fatty alcohols.
(3) Polyhydric alcohol esters. Ethylene glycol mono and di-fatty acid ester, diethylene glycol mono- and di-fatty acid esters, polyethylene glycol (200–6000) mono-and di-fatty acid esters, polypropylene glycol 2000 monooleate, polypropylene glycol 200 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.
(4) Wax esters such as beeswax, spermaceti, myristyl myristate, stearyl stearate and arachidyl behenate.
(5) Sterols esters, of which cholesterol fatty acid esters are examples thereof.
(6) Triglycerides such as sunflower seed oil, maleated sunflower seed oil, borage seed oil and safflower oil.

Hydrocarbons suitable as emollients include petrolatum, mineral oil, isoparaffins and hydrocarbon waxes such as polyethylene.

Starches are also suitable emollients. Typical of this class is tapioca and arabinogalactan.

Fatty acids may also be suitable as emollients. The fatty acids normally have from 10 to 30 carbon atoms. Illustrative of this category are pelargonic, lauric, myristic, palmitic, stearic, isostearic, hydroxystearic, oleic, linoleic, riconleic, arachidic, behenic and erucic acids.

Antiaging actives are useful as skin benefit agents. Included within this category are vitamins, retinoids and combinations thereof. Amounts of these materials may range from about 0.001 to about 20% by weight of the total composition. Suitable vitamins include ascorbic acid, Vitamin $B_6$, Vitamin $B_{12}$, tocopherol as well as salts and $C_1$–$C_{20}$ esters thereof. Suitable retinoids include retinoic acid as well as its $C_1$–$C_{22}$ esters and salts, retinol and $C_1$–$C_{22}$ fatty esters of retinol including retinyl linoleate.

Another class of antiaging actives are the alpha- and beta-hydroxycarboxylic acids and salts thereof. Representative of this group are glycolic acid, lactic acid, malic acid, hydroxyoctanoic acid, salicylic acid and mixtures of these as well as their salts and lactone derivatives. Suitable salts are the alkalimetal, ammonium and $C_1$–$C_{10}$ alkanol ammonium salts.

Antibacterials and fungicidals may be included as skin benefit agents. Representative of these categories are triclosan, tricloban, hexetidene, chlorhexadene, gluconates, zinc salts (e.g. zinc citrate and zinc phenolsulfonate) and combinations thereof.

Skin lighteners may be included under the skin benefit agents. Typical of this category are niacinamide, kojic acid, arbutin, vanillin, ferulic acid and esters thereof, resorcinol, hydroquinone, placental extract and combinations thereof.

Sunscreens may also be included as skin benefit agents. Particularly preferred are such materials as ethylhexyl p-methoxycinnamate, available as Parsol® MCX, and benzophenone-3, also known as Oxybenzone. Inorganic sunscreen actives may be employed such as microfine titanium dioxide, polyethylene and various other polymers. Amounts of the sunscreen agents will generally range from 0.1 to 30%, preferably from 2 to 20%, optimally from 4 to 10% by weight.

Adjunct functional agents may be incorporated into compositions of the present invention. These include electrolytes, thickeners and mixtures thereof. Amounts of these substances may range from about 0.1 to about 20%, preferably from about 0.3 to about 10% optimally between about 0.5 and about 5% by weight of the total composition.

Electrolytes may be selected from alkali, alkaline earth or ammonium salts of phosphates, silicates, halides, sulphates and mixtures thereof. Typical phosphates are potassium polymetaphosphate, sodium tripolyphosphate, sodium tetrapyrophosphate, sodium or potassium pyrophosphate and sodium hexametaphosphate. Most preferred is potassium polymetaphosphate available as Lipothix 100B® which is a 70:30 mixture of potassium polymetaphosphate and sodium bicarbonate, available from Lipo chemicals, Inc., Paterson, N.J. Preferred sulphates are the magnesium sulphates.

Thickeners which may improve afterfeel properties on skin include inorganic or organic substances. A particularly preferred inorganic thickener is sodium magnesium silicate commercially available as Optigel SH®. Organic thickeners include alginic acid as well as sodium and calcium alginates, sodium carboxymethyl cellulose, hydroxypropyl methylcellulose, hydroxypropyl cellulose, hydroxyethyl cellulose and combinations thereof. Most preferred is alginic acid commercially available as Kelacid® from Sud-Chemie Rheologicals, Louisville, Ky. Alginic acid is highly effective at removing the slimy feel associated with deposits of alkaline material which are not fully rinsed away from the skin. Amounts of the thickener may range from about 0.1 to about 20%.

Polysaccharides useful in this invention are dry solid anhydrous substances such as sorbitol, sugars, (such as trehalose) starches, modified starches (e.g. aluminum octenyl succinate) and mixtures thereof. Most preferred is sorbitol.

Deposition aids may also be incorporated in compositions of the present invention. These assist in depositing skin benefit agents onto the skin surface. Particularly effective are cationic monomers and polymers for this purpose. Most preferred for purposes of this invention are cationic guar gums such as Jaguar C13S® which is guar hydroxypropyltrimonium chloride. Amounts of the deposition aid may range from about 0.01 to about 1%, preferably from about 0.05 to about 0.5%, optimally from about 0.1 to about 0.3% by weight.

Advantageously an emotive agent such as a fragrance and/or botanical extract are included with the effervescent cleansing composition. Fragrances and botanicals are often liquids. For this reason it is necessary to uniformly distribute and allow absorption of liquid components into the solid powder. One method of best achieving this is to spray these liquids onto the solids. Amounts of the fragrance and/or liquid botanicals combined may be at levels from about 0.1 to about 3%, preferably from 0.5 to 2%, optimally from 0.8 to 1.5% by weight of the total composition.

The term "fragrance" is defined as a mixture of odoriferous components, optionally mixed with a suitable solvent diluent or carrier, which is employed to impart a desired odor. Particular preferred odoriferous components are cyclic and acyclic terpenes and terpenoids. These materials are based upon isoprene repeating units. Examples include alpha and beta pinene, myrcene, geranyl alcohol and acetate, camphene, dI-limonene, alpha and beta phellandrene, tricyclene, terpinolene, allocimmane, geraniol, nerol, linanool, dihydrolinanool, citral, ionone, methyl ionone, citronellol, citronellal, alpha terpineol, beta terpineol, alpha fenchol, borneol, isoborneol, camphor, terpinen-1-ol, terpin-4-ol, dihydroterpineol, methyl chavicol, anethole, 1,4 and 1,8 cineole, geranyl nitrile, isobornyl acetate, linalyl acetate, caryophyllene, alpha cedrene, guaiol, patchouli alcohol, alpha and beta santalol and mixtures thereof. Botanicals of particular use in the present invention include yarrow, chamomile, jasmine, lavender, horse chestnut, sage, thyme, yucca, coltsfoot and mixtures thereof.

Preservatives can desirably be incorporated into the cosmetic compositions of this invention to protect against the growth of potentially harmful microorganisms. Particularly preferred preservatives are phenoxyethanol, methyl paraben, propyl paraben, imidazolidinyl urea, sodium dehydroacetate and benzyl alcohol. The preservatives should be selected having regard for the sue of the composition and possible incompatibilities between the preservatives and other ingredients. preservatives are preferably employed in amounts ranging from 0.01% to 2% by weight of the composition.

Colorants may also be included in compositions of the present invention. These Substances may range from about 0.05 to about 5%, preferably between 0.1 and 3% by weight.

Skin surfaces against which articles of the present invention are useful include face, body, scalp, axilla and even legs/feet. When the article is a foot cleanser, it would be advantageous for the sachet on one of its sides to be coarse while a second of the sides may be soft and gentle. An abrasive non-woven flexible wall in a foot cleanser product is useful for rubbing against calluses while the second wall of the sachet remains smooth.

Articles according to the present invention may be formed in the following manner. In a preferred embodiment, a non-woven material is folded to form pleats by running the material through a folding device during or after non-woven manufacture. The pleats are held in place by adhesive tracks which can be a hot-melt glue or an adhesive tape. By way of example, first and second walls of a sachet are cut into a round or oval shape. The sachet is assembled by drawing a flat sheet of non-woven material onto a flat conveyer belt. Effervescent cleansing composition in dry solid form is dosed onto the sheet of material. Thereafter a section of pleated sheet is placed over the flattened sheet. Between the sheets a pouch is defined enclosing the effervescent cleansing composition. The pouch is then sealed along its perimeter. Cutters then separate one sealed section from another thereby forming the wiping article. Alternatively the cutting procedure can proceed that of the sealing step. One or more of the wiping articles are then packaged within a moisture impermeable outer package such as a laminated foil bag or box to prevent activation of the effervescent system during storage.

In a preferred embodiment the non-woven material forming the pleated wall is instructed from wood pulp/polyester blend manufactured in a spun lace process, and available from the DuPont Company as Sontara® S-9911 type. Most preferred as the non-pleated relatively more rigid material for the opposite wall of the sachet is a polyester/nylon blend with acrylate binder available from Freudenburg Corporation under the Vilene trademark. As an example, rigidity of the non-woven material forming the pleated wall can have a value ranging from about 110 to about 300, preferably from about 150 to about 210 in a machine manufactured direction and from about 10 to about 100, preferably from about 30 to about 50 in a cross machine direction. Rigidity is measured according to INDA (Association of the Non-Woven Fabrics Industry) standard test 90.0–75. Rigidity of the more rigid material for an opposite wall of the sachet may range from about 250 to about 800, preferably from about 400 to about 550 in a machine direction and from about 100 to about 300, preferably from about 200 to about 240 in a cross machine direction, with reference to the INDA standard test 90.0–75.

Ultrasonic welding may be employed as an alternative to heat-sealing of the first and second substrates together. Thread stitching, glue application or other closure mechanisms may also be utilized.

Effervescent compositions of the present invention preferably have all Components blended together. However, the invention can also be operative with multi-compartments or wherein the alkaline material and the acid material are stored separate from one another to avoid premature effervescence.

Except in the operating and comparative examples, or where otherwise explicitly indicated, all numbers in this description indicating amounts of material are to be Understood as modified by the word "about".

The term "comprising" is meant not to be limiting to any subsequently stated elements but rather to encompass non-specified elements of major or minor functional importance. In other words the listed steps, elements or options need not be exhaustive.

The following examples will more fully illustrate embodiments of this invention. All parts, percentages and proportions referred to herein and in the appended claims are by weight unless otherwise indicated.

EXAMPLE 1

An effervescent cleansing composition is prepared according to the formulation reported in Table I. Phase A is dry blended in a high speed shearing mixer. Fragrance is then sprayed onto the resultant powder as a Phase B. Three grams of the resultant powder are then placed into a two inch by three inch non-woven rayon sachet formed with a single pleat. All sides are closed by double stitching with thread.

TABLE I

| INGREDIENT | WEIGHT % |
|---|---|
| PHASE A | |
| Sodium Bicarbonate | 34.5 |
| Citric Acid (Anhydrous) | 40.4 |
| Sodium Cocoyl Isethionate (Powder) | 11.6 |
| Sodium Sesquicarbonate | 5.0 |
| Lipothix 100B ® (Potassium Polymetaphosphate/Bicarbonate 70:30) | 0.5 |
| Optigel SH ® (Sodium Magnesium Silicate) | 1.0 |
| Kelacid ® (Alginic Acid) | 1.0 |
| Sorbitol | 5.0 |
| PHASE B | |
| Fragrance | 1.0 |

EXAMPLE 2

Another effervescent cleansing composition is prepared according to the formulation reported in Table II.

TABLE II

| INGREDIENT | WEIGHT % |
|---|---|
| PHASE A | |
| Sodium Bicarbonate | 34.5 |
| Citric Acid (Anhydrous) | 40.4 |
| Sodium Cocoyl Isethionate (Powder) | 11.6 |
| Sodium Sesquicarbonate | 5.0 |
| Lipothix 100B ® (Potassium Polymetaphosphate/Bicarbonate 70:30) | 0.5 |
| Optigel SH ® (Sodium Magnesium Silicate) | 1.0 |
| Kelacid ® (Alginic Acid) | 1.0 |
| Sorbitol | 5.0 |
| Laracare A200 ® (arabinogalactan) | 1.0 |
| Ascorbic Acid | 0.5 |
| PHASE B | |
| Fragrance | 1.0 |

EXAMPLE 3

A face cleansing effervescent composition is prepared according to the formulation reported in Table III.

TABLE III

| INGREDIENT | WEIGHT % |
|---|---|
| PHASE A | |
| Sodium Bicarbonate | 33.6 |
| Citric Acid (Anhydrous) | 39.0 |

TABLE III-continued

| INGREDIENT | WEIGHT % |
|---|---|
| Sodium Cocoyl Isethionate (Powder) | 3.0 |
| Sodium Methyl Cocoyl Taurate | 6.0 |
| Sodium Lauryl Sulfate | 2.5 |
| Sodium Sesquicarbonate | 5.0 |
| Lipothix 100B ® (Potassium Polymetaphosphate/Bicarbonate 70:30) | 0.5 |
| Optigel SH ® (Sodium Magnesium Silicate) | 2.0 |
| Tapioca | 5.5 |
| Methyl Gluceth 20-Benzoate | 2.0 |
| Guar Hydroxypropyl Trimonium Chloride | 0.25 |
| PHASE B | |
| Fragrance | 0.65 |

EXAMPLE 4

A still further effervescent cleansing composition according to the present invention may be prepared according to the formulation reported under Table IV. Phase A is prepared by dry mixing of the ingredients in a high speed shear mixer. Three grams of resultant powder are placed into a two inch by three inch sachet of non-woven cotton polyester (50:50) formed with ten pleats on one side. The mesh size of the sachet walls is sufficient to allow transfer of dissolved ingredients. All sides of the sachet are welded by ultrasonic heat to insure against powder escaping from the sachet.

TABLE IV

| INGREDIENT | WEIGHT % |
|---|---|
| PHASE A | |
| Potassium Bicarbonate | 29.5 |
| Lactic Acid (Anhydrous) | 45.4 |
| Sodium Sulfosuccinate | 11.6 |
| Sodium Sesquicarbonate | 5.0 |
| Lipothix 100B ® (Potassium Polymetaphosphate/Bicarbonate 70:30) | 0.5 |
| Optigel SH ® (Sodium Magnesium Silicate) | 1.0 |
| Kelacid ® (Alginic Acid) | 1.0 |
| Sorbitol | 5.0 |
| PHASE B | |
| Fragrance | 1.0 |
| Licorice Extract | 0.1 |

EXAMPLE 5

Still another effervescent cleansing composition is prepared according to the formulation reported in Table V. The ingredients are dry blended in a high speed shearing mixer. Fragrance and herbal extract are sprayed onto the powder and further blended to achieve homogeneity. Three grams of the resultant powder are placed into a three inch diameter round sachet formed of non-woven polypropylene with one of the walls formed with 3 pleats. All sides are closed by convection heat sealing along the perimeter thereof.

TABLE V

| INGREDIENT | WEIGHT % |
|---|---|
| PHASE A | |
| Sodium Bicarbonate | 29.5 |
| Citraconic Acid (Anhydrous) | 45.4 |

TABLE V-continued

| INGREDIENT | WEIGHT % |
|---|---|
| Methyl Glucamide | 11.6 |
| Sodium Sesquicarbonate | 5.0 |
| Lipothix 100B ® (Potassium Polymetaphosphate/Bicarbonate 70:30) | 0.5 |
| Optigel SH ® (Sodium Magnesium Silicate) | 1.0 |
| Kelacid ® (Alginic Acid) | 1.0 |
| Sorbitol | 5.0 |
| PHASE B | |
| Fragrance | 0.9 |
| Yarrow | 0.1 |

EXAMPLE 6

Yet another face cleansing effervescent composition is prepared according to the formulation reported in Table VI.

TABLE VI

| INGREDIENT | WEIGHT % |
|---|---|
| PHASE A | |
| Sodium Bicarbonate | 32.3 |
| Citric Acid (Anhydrous) | 41.1 |
| PHASE B | |
| Guar Hydroxypropyl Trimonium Chloride | 0.4 |
| Lipothix 100B ® | 0.5 |
| Optijel SH ® | 2.0 |
| PHASE C | |
| Sodium Cocoyl Isethionate | 3.0 |
| Sodium Methyl Cocoyl Taurate | 6.0 |
| Sodium Lauryl Sulphate | 1.5 |
| Sodium Lauroyl Sarcosinate | 3.0 |
| PHASE D | |
| Sodium Sesquicarbonate | 4.0 |
| Tapioca | 4.7 |
| Sorbitol | 0.5 |
| Fragrance | 1.0 |

The foregoing description and examples illustrate selected embodiments of the present invention. In light thereof variations and modifications will be suggested to one skilled in the art, all of which are within the spirit and purview of this invention.

What is claimed is:

1. A cosmetic article for cleansing body surfaces, the article comprising:

a sachet having at least one water permeable wall, the sachet being sealed along all its perimeter, at least one pleat formed in at least one wall of the sachet; and an effervescent cleanser composition positioned within the sachet.

2. The article according to claim 1 wherein the pleat is a single pleat.

3. The article according to claim 1 wherein the at least one pleat ranges in number from 1 to about 50 pleats.

4. The article according to claim 1 wherein the sachet comprises opposite first and second walls, the second wall being non-pleated and formed of a material more rigid than that of the first wall.

5. The article according to claim 1 wherein the effervescent cleanser composition is an anhydrous dry solid comprising:

(i) from about 1 to about 80% of an alkaline material;

(ii) from about 0.5 to about 80% of an acid material; and (iii) from about 0.1 to about 30% of a surfactant.

6. The article according to claim 5 wherein the composition further comprises from about 0.01 to about 30% by weight of a skin benefit agent selected from the group consisting of emollients, anti-aging actives, antibacterials and fungicides, skin tighteners, sunscreens and mixtures thereof.

7. The article according to claim 5 wherein the surfactant is sodium cocoyl isethionate.

8. The article according to claim 5 wherein the acid is citric acid.

9. The article according to claim 5 wherein the composition further comprises from about 0.01 to about 1% by weight of a deposition aid which is a cationic monomer or polymer.

10. A method for cleansing skin comprising wetting with water a cosmetic article, generating foam from the article and wiping skin surfaces with the wetted article, the article comprising:

a sachet having at least one water permeable wall, the sachet being sealed along all its perimeter, at least one pleat formed in at least one wall of the sachet; and an effervescent cleanser composition positioned within the sachet.

* * * * *